(12) United States Patent
Bell (10) Patent No.: US 11,681,053 B1
(45) Date of Patent: Jun. 20, 2023

(54) METHODS, SYSTEMS, AND DEVICES FOR MONITORING CUMULATIVE RADIATION

(71) Applicant: Actev Motors, Inc., Mooresville, NC (US)

(72) Inventor: David Bundy Bell, Mooresville, NC (US)

(73) Assignee: ACTEV MOTORS. INC., Mooresville, NC (US)

( * ) Notice: Subject to any disclaimer, the term of this patent is extended or adjusted under 35 U.S.C. 154(b) by 210 days.

(21) Appl. No.: 17/314,432

(22) Filed: May 7, 2021

Related U.S. Application Data (60) Provisional application No. 63/102,387, filed on Jun. 12, 2020, provisional application No. 63/102,345, filed on Jun. 10, 2020.

(51) Int. Cl.
*G01T 1/02* (2006.01)
*G01T 1/20* (2006.01)
*G01T 1/24* (2006.01)

(52) U.S. Cl.
CPC ............ *G01T 1/026* (2013.01); *G01T 1/2018* (2013.01); *G01T 1/247* (2013.01)

(58) Field of Classification Search
None
See application file for complete search history.

(56) References Cited

U.S. PATENT DOCUMENTS

| | | | |
|---|---|---|---|
| 5,008,548 A * | 4/1991 | Gat | G01J 1/429 250/372 |
| 10,132,680 B1 * | 11/2018 | Isikman | G01J 1/18 |

FOREIGN PATENT DOCUMENTS

JP         H0518821 A  *  1/1993

* cited by examiner

*Primary Examiner* — Edwin C Gunberg
(74) *Attorney, Agent, or Firm* — NK Patent Law (57) ABSTRACT

Disclosed herein are methods, systems, and devices for monitoring cumulative radiation. In one embodiment, a device includes a photodiode; an integrating capacitor electrically coupled with the photodiode; a voltage discharge switch electrically coupled with the integrating capacitor; and amplifier circuitry electrically coupled with the photodiode and the integrating capacitor. The amplifier circuitry is configured to maintain a substantially zero bias voltage between an anode and a cathode of the photodiode monitoring the cumulative radiation. The integrating capacitor is configured to provide a delta voltage representative of radiation received since the beginning of a charge cycle of the integrating capacitor.

22 Claims, 4 Drawing Sheets

METHODS, SYSTEMS, AND DEVICES FOR MONITORING CUMULATIVE RADIATION

PRIORITY CLAIM

This application claims priority to U.S. Provisional Patent Application Ser. No. 63/102,345 filed Jun. 10, 2020, entitled "NOVEL LIGHT DOSIMETER CIRCUIT WITH WIDE DYNAMIC RANGE;" and U.S. Provisional Patent Application Ser. No. 63/102,387 filed Jun. 12, 2020, entitled "REMOTELY ACTIVATED WIRELESS LIGHT DOSIMETER." The disclosures of each of the aforementioned applications are incorporated herein by reference in their entireties.

TECHNICAL FIELD

The presently disclosed subject matter relates generally to sensor devices for environmental monitoring. More specifically; methods, systems, and devices are disclosed herein for light dosimetry applications.

BACKGROUND

Ultraviolet-C(UVC) ultraviolet disinfection systems have become popular in hospitals for the reduction of health care-associated infections (HAIs). Millions of patients and staff are affected by HAIs each year. These UVC ultraviolet disinfection systems broadcast high-intensity UVC light to permanently damage the ribonucleic acid (RNA) and deoxyribonucleic acid (DNA) in pathogens and thereby neutralize their ability to reproduce.

The coronavirus disease 2019 (COVID-19) pandemic has increased the awareness that pathogens (e.g. bacteria, viruses, and fungi) can easily transfer between people by surface contact. Consequently, the usage of UVC ultraviolet disinfection systems in hospitals has rapidly increased, and such UVC ultraviolet disinfection systems are now being deployed in various public locations to mitigate the transfer of pathogens.

As such, new and improved methods, devices, and systems for determining adequate disinfection are needed when using UVC ultraviolet disinfection systems.

SUMMARY

Disclosed herein are methods, systems, and devices for monitoring cumulative radiation. In one embodiment, a device includes a photodiode; an integrating capacitor electrically coupled with the photodiode; a voltage discharge switch electrically coupled with the integrating capacitor; and amplifier circuitry electrically coupled with the photodiode and the integrating capacitor. The amplifier circuitry is configured to maintain a substantially zero bias voltage between an anode and a cathode of the photodiode while monitoring the cumulative radiation. The integrating capacitor is configured to provide a delta voltage representative of radiation received since the beginning of a charge cycle of the integrating capacitor.

In some embodiments, the device may include analog-to-digital circuitry electrically coupled with the integrating capacitor. The analog-to-digital circuitry may be configured for determining when a voltage across the integrating capacitor has crossed a predetermined threshold. In certain embodiments the analog-to-digital circuitry may include a voltage comparator or the like.

In some embodiments, the voltage discharge switch may be configured for partially discharging the integrating capacitor upon receiving a reset signal. In certain embodiments, the voltage discharge switch may include a field effect transistor (FET) or the like.

In some embodiments, the device may further include temperature compensation circuitry electrically coupled with the analog-to-digital circuitry. The temperature compensation circuitry may be configured for modifying the predetermined threshold. In certain embodiments, the temperature compensation circuitry may include a diode configured for a needed temperature characteristic.

In some embodiments, the device may further include digital circuitry configured for providing the reset signal upon the analog-to-digital circuitry determining the voltage across the integrating capacitor has crossed the predetermined threshold.

In some embodiments, the digital circuitry may be configured for providing the reset signal upon determining a predetermined time interval has been exceeded and the voltage across the integrating capacitor has not crossed the predetermined threshold.

In some embodiments, the digital circuitry may be further configured for maintaining a count of a plurality of discharge cycles of the integrating capacitor.

In some embodiments, the device may further include a user interface electrically coupled with the digital circuitry. The user interface may be configured for displaying an estimate of a radiation dose received by a surface based on the count of the plurality of discharge cycles of the integrating capacitor.

In some embodiments, the user interface may be configured for receiving a request to reset the count of the plurality of discharge cycles of the integrating capacitor.

In some embodiments, the user interface may include a liquid crystal display (LCD) configured for displaying the estimate of a radiation dose received by a surface based on the count of the plurality of discharge cycles of the integrating capacitor. Additionally, the user interface may include a momentary contact switch configured for receiving the request to reset the count of the plurality of discharge cycles of the integrating capacitor.

In some embodiments, the device may further include a processor, a memory electrically coupled with the processor; and a wireless communication interface electrically coupled with the processor.

In some embodiments, the wireless interface may be compliant to a least one version of a Bluetooth communication protocol or the like. In certain embodiments, the Bluetooth communication protocol may be configured for supporting real-time location systems. In other embodiments, the wireless interface may be compliant with a least one version of an 802.11 Wi-Fi protocol or the like. In still other embodiments, the wireless interface may compliant to a least one version of a ZigBee® protocol, a Z-wave®, or the like. In still other embodiments, the wireless interface may compliant to a least one version of an ultra-wideband (UWB) protocol or the like. In certain embodiments, the wireless interface may be compliant with a Long Range (LoRa®) protocol.

In some embodiments, the wireless communication interface may be configured for transmitting data associated with the cumulative radiation received by the photodiode. In certain embodiments, the wireless interface may be configured to receive a command to provide the reset signal.

In some embodiments, the wireless communication interface may be configured for being activated from a standby low-power state to an active state upon the cumulative radiation received by the photodiode exceeding a predetermined threshold.

In some embodiments, the photodiode may be configured for detecting ultraviolet radiation. In certain embodiments, the photodiode may be configured for detecting ultraviolet-C(UVC) radiation. In other embodiments, the photodiode may be configured for detecting visible light. In still other embodiments, the photodiode may be configured for detecting infrared radiation.

In some embodiments, the photodiode may be an Aluminum Gallium Nitride based Schottky diode.

In some embodiments, the device may further include a narrowband optical filter having a passband of at least 250 nanometers to 260 nanometers. In certain embodiments, the narrowband optical filter may have a passband of at least 220 nanometers to 280 nanometers.

In some embodiments, the narrowband optical filter may be integrated with the photodiode.

In some embodiments, the device may be implemented within a light dosimeter, a power meter, or the like.

In another embodiment, a method of operating a device for measuring cumulative radiation is disclosed. The method includes charging an integrating capacitor using a photodiode. A voltage across the integrating capacitor is representative of radiation received during a charge cycle of the integrating capacitor. The method further includes maintaining a substantially zero bias voltage between an anode and a cathode of the photodiode using amplifier circuitry electrically coupled with the photodiode and the integrating capacitor, and determining when the voltage across the integrating capacitor has crossed a predetermined threshold. The method further includes discharging the voltage across the integrating capacitor using a voltage discharge switch electrically coupled with the integrating capacitor upon receiving a reset signal, and maintaining a count of a plurality of discharge cycles of the integrating capacitor. Additionally, the method includes displaying on a user interface an estimate of a radiation dose received by a surface based on a count of a plurality of discharge cycles of the integrating capacitor.

In some embodiments, the method may further include receiving from the user interface a request to reset the count of the plurality of discharge cycles of the integrating capacitor.

In some embodiments, the method may further include detecting (UVC) radiation using the photodiode. In other embodiments, the method may further include detecting visible light using the photodiode. In still other embodiments, the method may further include detecting infrared radiation using the photodiode.

In some embodiments, the method may further include modifying the predetermined threshold based on temperature using temperature compensation circuitry.

The features and advantages described in this summary and the following detailed description are not all-inclusive. Many additional features and advantages will be apparent to one of ordinary skill in the art in view of the drawings, specification, and claims presented herein.

BRIEF DESCRIPTION OF THE DRAWINGS

The present embodiments are illustrated by way of example and are not intended to be limited by the figures of the accompanying drawings. In the drawings.

DETAILED DESCRIPTION

The following description and drawings are illustrative and are not to be construed as limiting. Numerous specific details are described to provide a thorough understanding of the disclosure. However, in certain instances, well-known or conventional details are not described in order to avoid obscuring the description. References to "one embodiment" or "an embodiment" in the present disclosure can be, but not necessarily are, references to the same embodiment and such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification.

Methods, devices, and systems are disclosed herein for measuring cumulative radiation. For example, such methods devices and systems may be used for determining adequate disinfection when using ultraviolet-C(UVC) disinfection systems. Most UVC disinfection systems use high-power low-pressure mercury lamps to produce 254 nanometer (nm) wavelength UV light. Although different types of pathogens require different dose levels for sufficient disinfection, at least 99.99% of most pathogens may be neutralized with a 254 nanometer (nm) UVC dose of 50 millijoules per square centimeter (mJ/cm$^2$). Consequently, this 50 mJ/cm$^2$ dose is often the minimum target dose used for disinfection.

In order to ensure disinfection, it is necessary to verify that UVC disinfection equipment is delivering the minimum target dose to surfaces that are likely contacted by people. Surfaces that are in direct line-of-sight of the lamps generally receive sufficient dose. However, light intensity reduces with distance from the lamps so distant surfaces will receive lower doses. Additionally, UVC lamp power output diminishes with age and must be taken into consideration. Because of these variables, UVC equipment is usually configured to over-dose UVC light to ensure that surfaces receiving the lowest UVC intensity still receive at least the minimum target dose.

However, significant UVC over-dosing has two downsides. Firstly, additional expensive UVC disinfection equipment may need to be purchased if each disinfection unit is required to spend more time in every room. Secondly, fabrics, woods, and plastics can deteriorate with long-term UVC exposure. As such, overdosing may require more frequent replacement of curtains, bedding, furniture, and even equipment.

UVC light dosimeters may be used to verify that sufficient doses are delivered to each surface. Currently, two different types of UVC light dosimeters are utilized. The first type is laboratory type instruments. These are expensive and not suitable for permanent mounting on walls and/or large scale distribution across facilities. The second type is single-use cards (e.g. approximately the size of a playing card) that gradually change color when dosed. However these single-use cards are imprecise and do not provide a numeric dose result.

Therefore, the need exists for a UVC light dosimeter that is accurate and clearly displays a numeric dose result. In addition, the UVC light dosimeter must be sufficiently low cost to allow users of UVC disinfection equipment to affix many dosimeters in a wide range of locations to permit verification that sufficient UVC doses are being delivered.

A UVC light dosimeter should also maintain accuracy over a wide power dynamic range. A dosimeter located close to a UVC lamp may receive 100 times the power of a dosimeter located in a distant shadowed area. However, both dosimeters must deliver accurate total dose measurements. Additionally, a UVC dosimeter should be sufficiently small to permit attachment to walls and equipment in rooms being disinfected by UVC equipment. The UVC dosimeter should be battery powered so no power cable is required, and ideally be capable of operating for one year or more on a single alkaline cell to eliminate the need for frequent battery replacements.

As such, new and improved methods, devices, and systems are disclosed as follows that may be used to implement a UVC light dosimeter as described in the preceding paragraphs.

Figure 1:
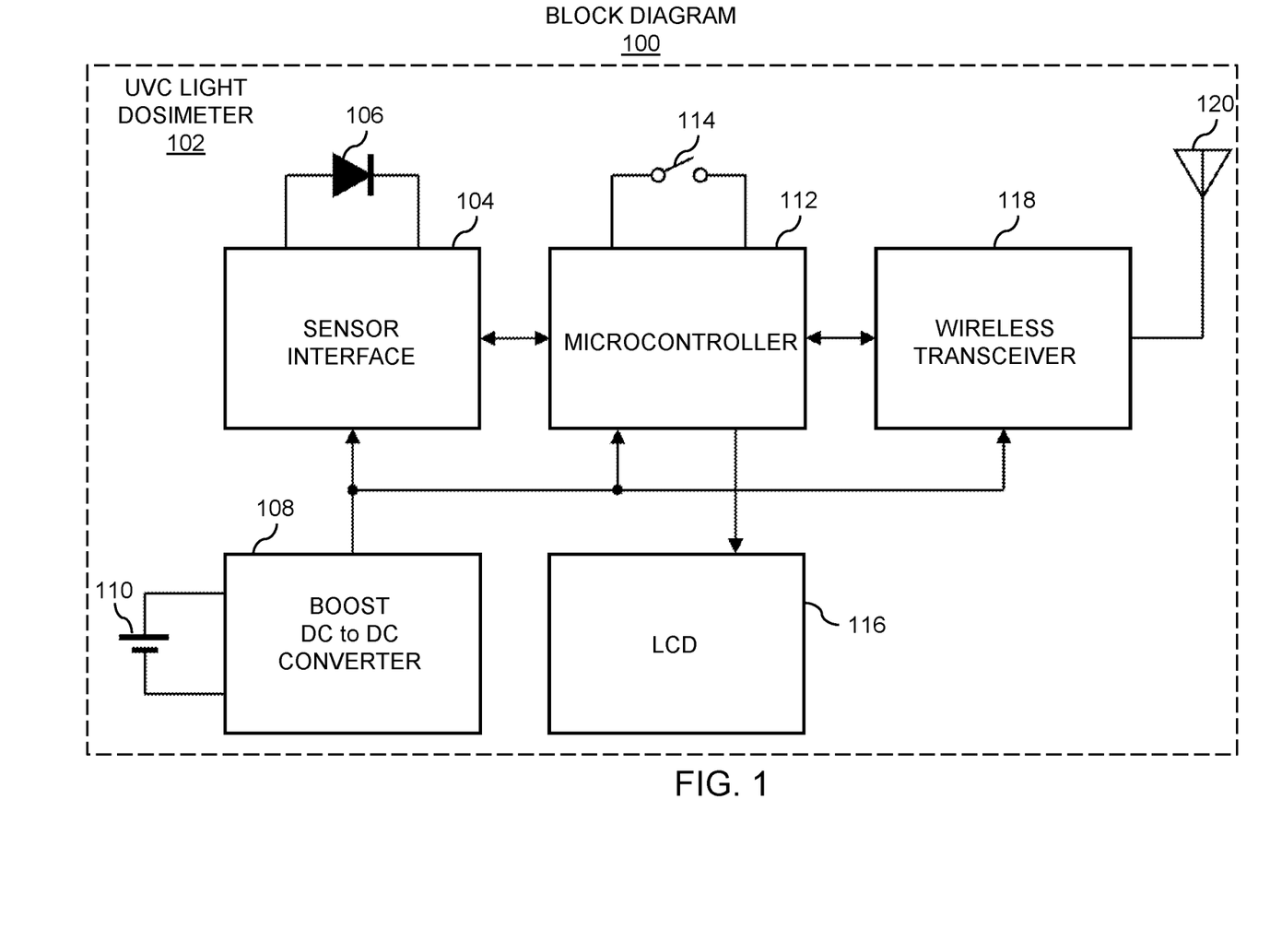
FIG. 1 depicts a block diagram illustrating an ultraviolet-C(UVC) light dosimeter in accordance with embodiments of the present disclosure.

FIG. 1 depicts a block diagram 100 illustrating a UVC light dosimeter 102 (i.e. device) in accordance with embodiments of the present disclosure. The UVC light dosimeter 102 includes a sensor interface 104. The sensor interface 104 includes a photodiode 106 for detecting UVC light representative of UVC light applied to a surface where the UVC light dosimeter 102 is positioned. The photodiode 106 may be Schottky photodiode, a PN photodiode, a P-I-N photodiode, an avalanche photodiode, or the like. In certain embodiments, the photodiode 106 may be an Aluminum Gallium Nitride based Schottky diode integrated with an integral narrow-band optical filter configured to pass 220 nanometers (nm) to 280 nm wavelength UVC ultraviolet light. In other embodiments, the photodiode 106 may be replaced with other types of detectors (e.g. a radio frequency detector diode, a faraday cup, or the like).

The sensor interface 104 is powered by a boost direct current (DC) to DC converter 108. In certain embodiments, the boost DC to DC converter 108 may include a plurality of DC to DC converters providing a plurality of voltages (e.g. 3.3 volts and 5.0 volts). A battery 110 provides a DC voltage input to the DC to DC converter 108. The battery 110 may be a single-cell alkaline battery providing approximately 1.5 volts DC. In some embodiments, the battery 110 may be an AA form factor battery, an AAA form factor battery, a ½ AA form factor battery, a ½ AAA form factor battery, or the like. The DC to DC converter 108 may be configured to provide approximately 5 volts DC.

The sensor interface 104 is electrically coupled with a microcontroller 112 (i.e. digital circuitry; and/or memory and processor). The microcontroller 112 is electrically coupled with a reset switch 114 (i.e. a portion of a user interface). Additionally, the microcontroller 112 is electrically coupled with a liquid crystal display (LCD) 116 (i.e. another portion of the user interface). The microcontroller 112 may be a low-power controller capable of directly driving the LCD 116. The reset switch 114 is configured (via the microcontroller 112) to reset a most recent radiation dose value displayed on the LCD 116. The DC to DC converter 108 also provides the DC voltage to the microcontroller 112 and the LCD 116.

In certain embodiments, the UVC light dosimeter 102 includes a wireless communication interface provided by a wireless transceiver 118 electrically coupled with the microcontroller 112. The wireless transceiver 118 is also electrically coupled with an antenna 120. In certain embodiments, the wireless transceiver 118 may be integrated with the microcontroller 112. The DC to DC converter 108 also provides the DC voltage to the wireless transceiver 118. The wireless communication interface may compliant to a least one version of a Bluetooth communication protocol or the like. Additionally the Bluetooth communication protocol may be configured for supporting real-time location systems. In other embodiments, the wireless communication interface may be compliant with at least one version of an 802.11 Wi-Fi protocol, a ZigBee protocol, a Z-wave protocol, a Long Range (LoRa) protocol, an ultra-wideband (UWB) protocol, a cellular protocol, or the like. The cellular protocol may include 2G, 3G, 4G, and/or 5G technologies. The 802.11 Wi-Fi protocol may include 802.11a, 802.11b/g/n, and/or 802.11ac technologies. In certain embodiments, the UVC light dosimeter 102 may be configured to operate as a part of a mesh network (having routing capability) via the wireless communication interface.

The wireless communication interface allows the UVC light dosimeter 102 to communicate with disinfection equipment. This capability provides real-time dose data and permits disinfection to terminate once predetermined dosage levels have been reached. Additionally, the wireless communication interface may communicate with a facility's information technology (IT) network. As such, periodic dosage readings may be automatically recorded and stored for statistical analysis and quality assurance purposes. The periodic dosage readings may be used to determine when a lamp of a given disinfection unit has degraded and replacement is required.

In certain embodiments, the disinfection equipment may send commands to the UVC light dosimeter 102 via the wireless communication interface. The commands may include disabling the wireless transceiver 118 when a disinfection cycle has ended and/or changing various configuration settings (e.g., resetting dose value, setting UVC alarms, or the like) on the UVC light dosimeter 102.

In the embodiment where the wireless communication is compliant to a Bluetooth communication protocol, the UVC light dosimeter 102 may be able to directly pair with the disinfection equipment. Additionally, the pairing may be facilitated by a mobile device such as a smartphone having Bluetooth capability. The Bluetooth protocol's real time location services (RTLS) capability may also be used to accurately measure the distance between the disinfection equipment and the UVC light dosimeter 102. The distance combined with dosimeter measured UVC intensity may be used to estimate the UVC power delivered by the disinfection equipment and track lamp degradation over time.

In some embodiments, the wireless communication interface may only be enabled when a given dosage is reached and/or on a periodic interval by the microcontroller 112. In such embodiments, battery life may be extended.

For example, the sensor interface 104 (and the microcontroller 112) may always be powered to detect a preset threshold of UVC light. Once the preset threshold is detected, then microcontroller 112 may enable wireless transceiver 118 and establish communication with the UVC disinfection equipment. In certain embodiments, the preset threshold may be approximately 4 microwatts per square centimeter (uW/cm$^2$). The preset threshold may also be programmable by a user of the UVC light dosimeter 102.

Additionally, the disinfection equipment may signal the UVC light dosimeter 102 that UVC disinfection is beginning other than just detecting the UVC light. For example, infrared light, sound, or other radio interface may be used to begin measurements and/or power on the wireless transceiver 118. In certain embodiments, the wireless transceiver 118 may only support a wireless transmitter (i.e. no wireless receiver). In this scenario, the wireless communication interface only transmits when the minimum dose has been reached and/or the UFC light dosimeter 102 has reset.

Figure 2:
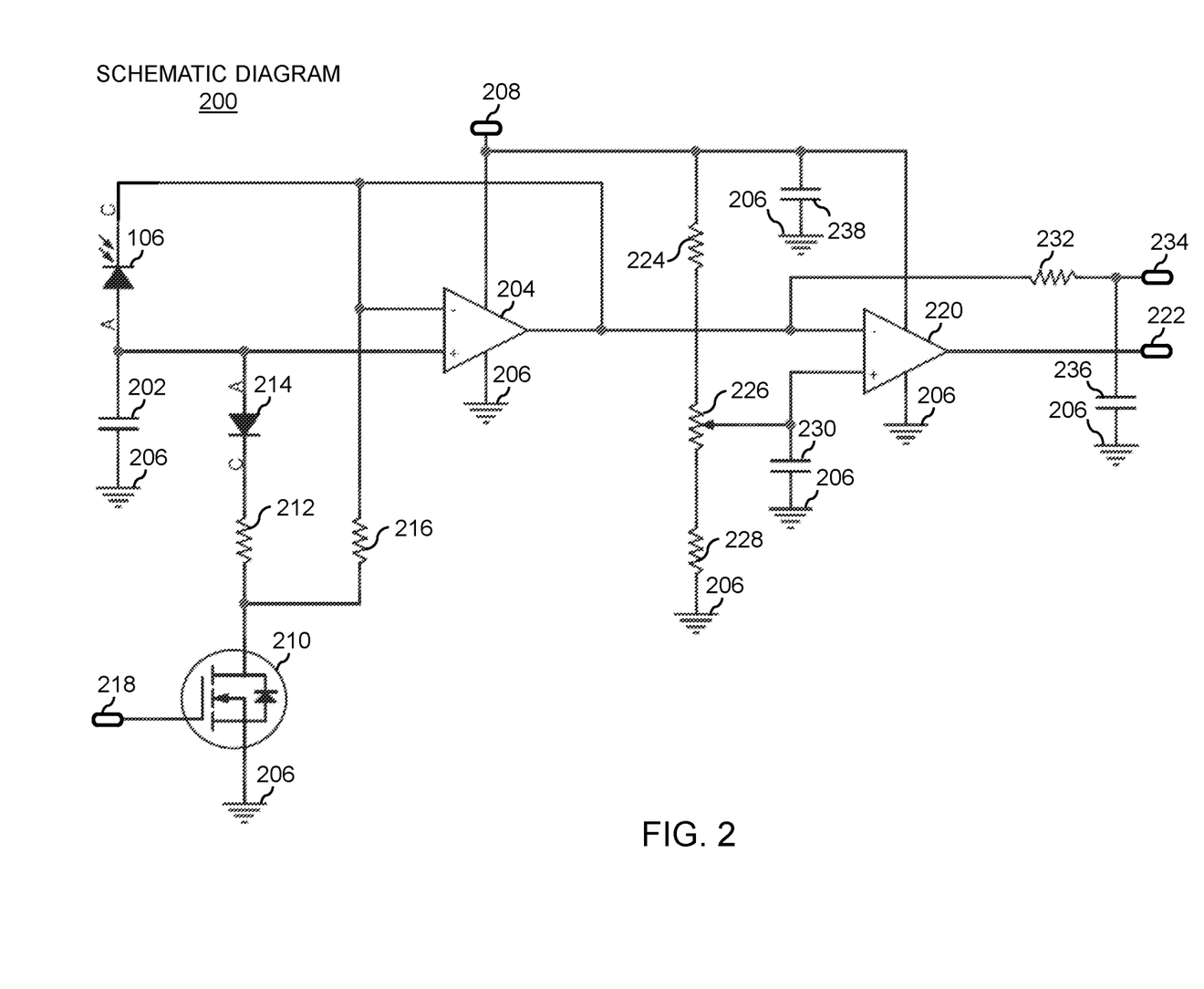
FIG. 2 depicts an electrical schematic illustrating a sensor interface circuit implemented in the UVC light dosimeter of FIG. 1 in accordance with embodiments of the present disclosure.

FIG. 2 depicts an electrical schematic 200 illustrating the sensor interface 104 implemented in the UVC light dosimeter 102 of FIG. 1 in accordance with embodiments of the present disclosure. The sensor interface 104 is configured for a high dynamic range and accuracy while operating on low power. An anode of the photodiode 106 is electrically coupled with an integrating capacitor 202. The anode of the photodiode 106 is also electrically coupled with a high impedance non-inverting input of an operational amplifier 204 (i.e. amplifier circuitry). The integrating capacitor 206 is also electrically coupled with a ground 206. A low impedance output of the operational amplifier 204 is electrically coupled with a high impedance inverting input of the operational amplifier 204 in a voltage follower configuration. A cathode of the photodiode 106 is also electrically coupled with the high impedance inverting input of the operational amplifier 204. DC power 208 is provided by the boost DC to DC converter 108 of FIG. 1 to a positive power supply input of the operational amplifier 204. The ground 206 is also electrically coupled with the negative power supply input of the operational amplifier 204.

The sensor interface 104 is configured to maintain an approximately zero voltage bias across the photodiode 106 due to the voltage follower configuration of the operational amplifier 204. The zero voltage bias minimizes any dark current (i.e. current that flows with no detected photons) that may be produced by the photodiode 106. The integrating capacitor 202 accumulates charge produced by the photodetector (i.e. photons creating electron hole pairs). Voltage across the integrating capacitor 202 is sensed using the operational amplifier 204 (i.e. amplifier circuitry). This type of configuration produces current flow in the reverse direction (current flowing out of the anode of the photodiode 106) when UVC photons are detected. In certain embodiments, the current flow may be as low as 140 pico-amps (pA) for a UVC intensity of 1 uW/cm$^2$.

Under operation, the current flow out of the photodiode 106 charges the integrating capacitor 202. Consequently, the voltage across integrating capacitor 202 increases in relation to the total UVC light dose received by the photodetector 106.

The sensor interface 104 is configured such that any current into or out of the integrating capacitor 202, other than the current flow out of the photodiode 106, is extremely low level. As such, operational amplifier 204 is configured to have an extremely low input bias current for the high impedance non-inverting input. Additionally, the integrating capacitor 202 has an extremely low leakage current. In certain embodiments, the integrating capacitor 202 may be constructed using a polypropylene film or a similar low leakage dielectric material.

A drain of a metal oxide semiconductor field-effect transistor (MOSFET) 210 (i.e. a voltage discharge switch) is electrically coupled with a first discharge resistor 212. The discharge resistor 212 is electrically coupled with a cathode of a discharge diode 214. An anode of the discharge diode 214 is electrically coupled with the integrating capacitor 202. A second discharge resistor 216 is coupled between the drain of the MOSFET 210 and the high impedance non-inverting input of the operational amplifier 204. A reset input port 218 is electrically coupled with a gate of the MOSFET 210 and electrically coupled with the microcontroller 112. The reset input port 218 is configured to receive a reset signal from the microcontroller 112. A source of the MOSFET 210 is electrically coupled with the ground 206. Upon receiving the reset signal from the microcontroller, the MOSFET 210 is turned on and the integrating capacitor 202 is discharged.

The off-state leakage current of the MOSFET 210 may exceed the current delivered by the photodiode 106 under low UVC power conditions. As such, electrically coupling the drain of MOSFET 210 directly to the integrating capacitor 202 could render the sensing interface 104 insensitive to low UVC power. The combination of the discharge resistor 216, the discharge resistor 212, and discharge diode 214 keep the voltage across the discharge diode 214 at nearly zero when MOSFET 210 is off, even though the MOSFET 210 has a small amount of leakage current present. Discharge diode 214 is a very low leakage type. With nearly zero voltage across discharge diode 214, leakage current is diminished to levels well below the minimum detector current. As such, low UVC power sensitivity of the UVC light dosimeter is 102 is preserved.

The output of the operational amplifier 204 is electrically coupled with an inverting input of a voltage comparator 220 (e.g. an analog-to-digital converter). The output of the operational amplifier 220 is approximately the same as the voltage on the integrating capacitor 202. An output of the voltage comparator 220 is electrically coupled with an interrupt output port 222 that is electrically coupled with the microcontroller 112. DC power 208 is provided by the boost DC to DC converter 108 of FIG. 1 to a positive power supply input of the voltage comparator 220. The ground 206 is also electrically coupled with the negative power supply input of the voltage comparator 220. In some embodiments, an analog-to-digital converter embedded in the microcontroller 112 may be used to replace the voltage comparator 220.

A first threshold resistor 224 is electrically coupled between the DC power 208 and a calibration potentiometer 226. A second threshold resistor 228 is electrically between the calibration potentiometer 226 and the ground 206. A center wiper of the calibration potentiometer 226 is electrically coupled with a non-inverting input of the comparator 220 and provides a threshold voltage for comparison against the voltage on the integrating capacitor 202. A filter capacitor 230 is electrically coupled between the center wipe of the calibration potentiometer 220 and the ground 206. The filter capacitor 230 is configured to provide a low noise and stable threshold voltage to the non-inverting input of the comparator 220.

When the voltage on the inverting input of voltage comparator 220 rises above the threshold voltage on the non-inverting input, the output of comparator 220 is pulled to ground. This creates an interrupt signal via the interrupt output port 222 to the microcontroller 112. Upon receipt of the interrupt signal, the microcontroller 112 performs two operations. First, it asserts the reset signal via reset input port 218, turning on MOSFET 210, and discharging the integrating capacitor 220 through the discharge diode 214 and discharge resistor 212. A pulse of approximately 200 microseconds (us) duration may be applied to discharge the integrating capacitor 202. Secondly, the microprocessor 112 increments a counter recording a number of interrupt signals received in order to calculate a total UVC dose received. The microcontroller 112 may also activate the wireless interface 118 when a minimum dose is reached in addition to displaying the total UVC light dose on the LCD 116 (i.e. a user interface).

The calibration potentiometer 226 may be adjusted during manufacturing calibration or in the field, such that each interrupt signal represents a fixed dose energy value.

A monitor resistor 232 is electrically coupled between the output of the operational amplifier 204 and a monitor port 234. A monitor capacitor 236 is coupled between the monitor port 234 and the ground 206. The monitor port 232 may be used during a calibration process of the UCV light dosimeter 102 using the calibration potentiometer 226.

Additionally, a filter capacitor 238 is electrically coupled between the DC power 208 and the ground 206, and is configured to remove noise on DC power 208.

Although the photodiode 106 may include a narrow-band optical filter to reject visible light, bright ambient light conditions will still produce a small amount of detected current. In order to prevent such invalid current from being integrated over a long period of time, the microcontroller 112 creates a "dead band" to reject power below 4uW/cm$^2$. This is implemented by a timeout condition whereby the integrating capacitor 202 is automatically discharged an interrupt signal has not occurred for a length of time representing a UVC power level below 4 uW/cm$^2$.

The discharge diode 214 creates a voltage drop when discharging the integrating capacitor 202. As such, the integrating capacitor 202 is discharged to a voltage level slightly above ground potential. The voltage drop across discharge diode 214 during discharging is somewhat temperature dependent. In certain embodiments a similar diode (not shown in FIG. 2) may be placed in a forward biased configuration between the second threshold resistor 228 and the ground 206. Any temperature impact of the discharge diode 214 may be at least partially compensated by a voltage drop across the similar diode. In still other embodiments, the similar diode may be placed in a forward biased configuration between second threshold resistor 228 and the calibration trimmer potentiometer 226.

As such, the UVC light dosimeter 102 of FIG. 1 and FIG. 2 is capable of accurate UVC dose measurements over a 10,000:1 UVC power range (4 uW/cm$^2$ to 40,000 uW/cm$^2$). The photodiode 106 may have a sensor field of view of approximately 100 degrees. Additionally, the LCD 116 may have a dosage range up to 199 mJ/cm$^2$ and the wireless communication interface may have a dosage range up to 65,535 mJ/cm$^2$.

In some embodiments, the UVC light dosimeter 102 when using a single AAA size alkaline cell for battery 110 may operate for over a year without needing to be replaced.

In summary, the sensor interface 104 of FIG. 2 while under control of the microcontroller 112 of FIG. 1 maximizes measurement dynamic range while still maintaining accuracy within the sensor interface 104 and using minimal battery power from the battery 110.

Figure 3:
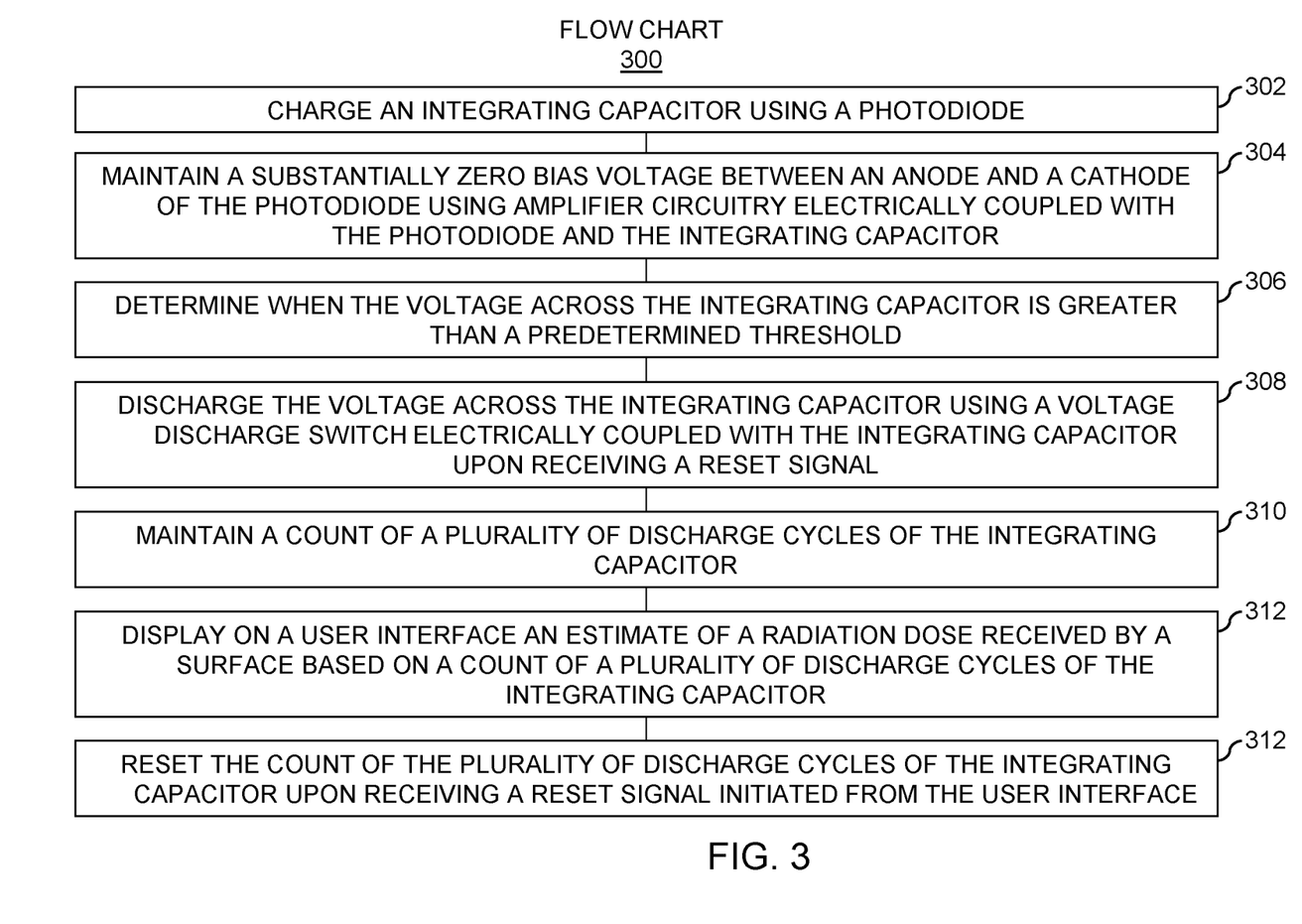
FIG. 3 depicts a flow chart illustrating a method for operating the UVC light dosimeter of FIG. 1 and FIG. 2 in accordance with embodiments of the present disclosure.

FIG. 3 depicts a flow chart 300 illustrating a method for operating a UVC light dosimeter (e.g. the UVC light dosimeter 102 of FIG. 1 and FIG. 2) in accordance with embodiments of the present disclosure.

In step 302, the method includes charging an integrating capacitor using a photodiode (e.g. the integrating capacitor 202 and the photodiode 106 of FIG. 1 and FIG. 2).

In step 304, the method further includes maintaining a substantially zero bias voltage between an anode and a cathode of the photodiode using amplifier circuitry electrically coupled with the photodiode and the integrating capacitor;

In step 306, the method further includes determining when the voltage across the integrating capacitor has crossed a predetermined threshold (e.g. the voltage comparator 220 of FIG. 2).

In step 308, the method further includes discharging the voltage across the integrating capacitor using a voltage discharge switch (e.g. the MOSFET 210 of FIG. 2) electrically coupled with the integrating capacitor upon receiving a reset signal.

In step 310, the method further includes maintaining a count of a plurality of discharge cycles of the integrating capacitor using digital circuitry (e.g. the microcontroller 112 of FIG. 2).

In step 312, the method further includes displaying on a user interface (e.g. the LCD 116 of FIG. 1) an estimate of a radiation dose received by a surface based on a count of a plurality of discharge cycles of the integrating capacitor.

In some embodiments not shown in flow chart 300, the method may further include receiving from the user interface (e.g. the reset switch 114 of FIG. 1) a request to reset the count of the plurality of discharge cycles of the integrating capacitor.

Figure 4:
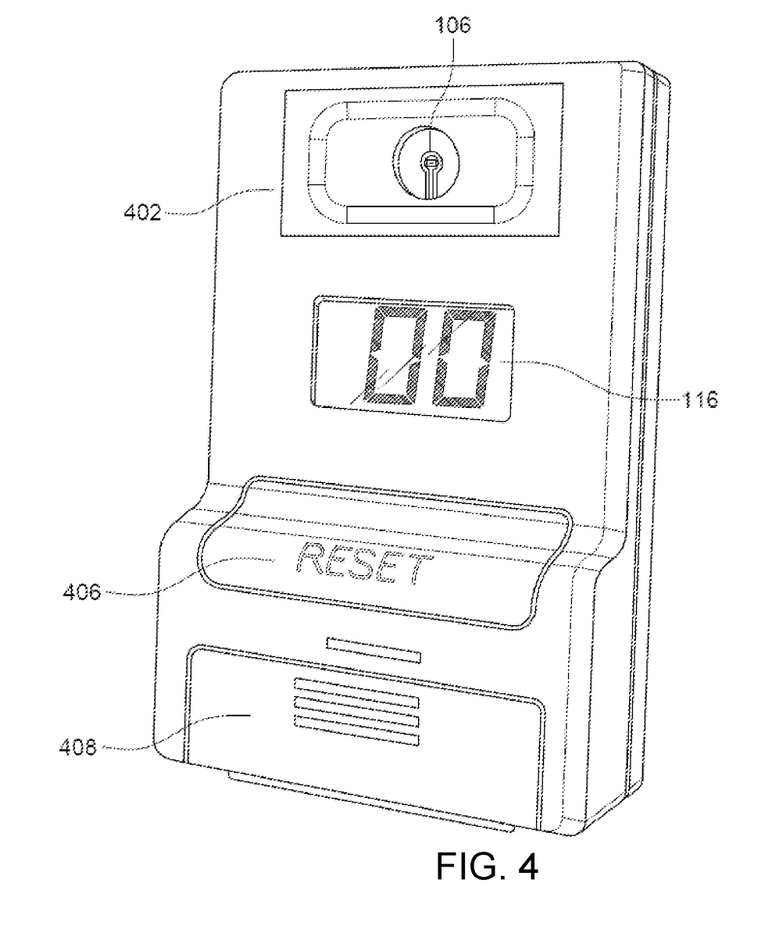
FIG. 4 depicts a diagram illustrating the UVC light dosimeter of FIG. 1 including a mechanical enclosure in accordance with embodiments of the present disclosure.

FIG. 4 depicts a diagram 400 illustrating the UVC light dosimeter of FIG. 1 including a mechanical enclosure 402 in accordance with embodiments of the present disclosure. A printed circuited board (PCB) positioned within the mechanical enclosure 402 includes the sensor interface circuitry 104, the photo diode 106, the boost DC to DC converter 108, the microcontroller 112, the battery 110 (and a battery holder), the LCD 116, and the reset switch 114 of FIG. 1. In certain embodiments, the PCB also includes the wireless transceiver 118 and the antenna 120 of FIG. 1. The mechanical enclosure includes a reset button 406 mechanically coupled with the reset switch 114. The mechanical enclosure 402 includes a first window exposing the photodiode 106 of FIG. 1 and FIG. 2. The mechanical enclosure 402 also includes a second window exposing the LCD 116 of FIG. 1. Additionally, the mechanical enclosure 402 includes a battery compartment door 408 configured for allowing replacement of the battery 110 of FIG. 1. In certain embodiments, the mechanical enclosure 402 may have dimensions of approximately 81 millimeters (mm) by 52 mm by 23 mm. The mechanical enclosure 402 may have an adhesive for wall mounting (e.g. a 3M Command™ strip). In certain embodiments, a mechanical holder (not shown in FIG. 4) may be used with the adhesive for wall mounting. The mechanical holder may be configured to support the mechanical enclosure 402 to allow easy removal of the mechanical enclosure for battery replacement and/or other maintenance.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including object oriented and/or procedural programming languages. For example, programming languages may include, but are not limited to: Ruby, JavaScript, Java, Python, Ruby, PHP, C, C++, C#, Objective-C, Go, Scala, Swift, Kotlin, OCaml, or the like.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device comprising:
   a photodiode;
   an integrating capacitor electrically coupled with the photodiode;
   a voltage discharge switch electrically coupled with the integrating capacitor;
   analog-to-digital circuitry electrically coupled with the integrating capacitor;
   temperature compensation circuitry electrically coupled with the analog-to-digital circuitry; and
   amplifier circuitry electrically coupled with the photodiode and the integrating capacitor, wherein:
   the amplifier circuitry is configured to maintain a substantially zero bias voltage between an anode and a cathode of the photodiode while monitoring cumulative radiation;
   the integrating capacitor is configured to provide a delta voltage representative of radiation received during a charge cycle of the integrating capacitor;
   the analog-to-digital circuitry is configured for determining when a voltage across the integrating capacitor has crossed a predetermined threshold;
   the temperature compensation circuitry is configured for modifying the predetermined threshold; and
   the voltage discharge switch is configured for partially discharging the integrating capacitor upon receiving a reset signal.

2. The device of claim 1, wherein the photodiode is an Aluminum Gallium Nitride based Schottky diode.

3. The device of claim 1, wherein the device is implemented within at least one of a light dosimeter and a power meter.

4. A device comprising:
   a photodiode;
   an integrating capacitor electrically coupled with the photodiode;
   a voltage discharge switch electrically coupled with the integrating capacitor;
   analog-to-digital circuitry electrically coupled with the integrating capacitor;
   digital circuitry; and
   amplifier circuitry electrically coupled with the photodiode and the integrating capacitor, wherein:
   the amplifier circuitry is configured to maintain a substantially zero bias voltage between an anode and a cathode of the photodiode while monitoring cumulative radiation;
   the integrating capacitor is configured to provide a delta voltage representative of radiation received during a charge cycle of the integrating capacitor;
   the analog-to-digital circuitry is configured for determining when a voltage across the integrating capacitor has crossed a predetermined threshold;
   the voltage discharge switch is configured for partially discharging the integrating capacitor upon receiving a reset signal; and
   the digital circuitry is configured for providing the reset signal upon the analog-to-digital circuitry determining the voltage across the integrating capacitor has crossed the predetermined threshold.

5. The device of claim 4, wherein the digital circuitry is configured for providing the reset signal upon determining a predetermined time interval has been exceeded and the voltage across the integrating capacitor has not crossed the predetermined threshold.

6. The device of claim 5, wherein the digital circuitry is further configured for maintaining a count of a plurality of discharge cycles of the integrating capacitor.

7. The device of claim 6 further comprising a user interface electrically coupled with the digital circuitry, and the user interface is configured for displaying an estimate of a radiation dose received by a surface based on the count of the plurality of discharge cycles of the integrating capacitor.

8. The device of claim 7, wherein the user interface is configured for receiving a request to reset the count of the plurality of discharge cycles of the integrating capacitor.

9. The device of claim 8, wherein the user interface comprises:
   a liquid crystal display configured for displaying the estimate of the radiation dose received by the surface based on the count of the plurality of discharge cycles of the integrating capacitor; and
   a momentary contact switch configured for receiving the request to reset the count of the plurality of discharge cycles of the integrating capacitor.

10. The device of claim 4, wherein the device is implemented within at least one of a light dosimeter and a power meter.

11. The device of claim 4, wherein the photodiode is an Aluminum Gallium Nitride based Schottky diode.

12. A device comprising:
    a photodiode;
    an integrating capacitor electrically coupled with the photodiode;
    a voltage discharge switch electrically coupled with the integrating capacitor;

a processor;

a memory electrically coupled with the processor; and a wireless communication interface electrically coupled with the processor; and amplifier circuitry electrically coupled with the photodiode and the integrating capacitor, wherein:

the amplifier circuitry is configured to maintain a substantially zero bias voltage between an anode and a cathode of the photodiode while monitoring cumulative radiation;

the integrating capacitor is configured to provide a delta voltage representative of radiation received during a charge cycle of the integrating capacitor;

the wireless communication interface is configured for:

activating from a standby low-power state to an active state upon determining a cumulative radiation dose received by the photodiode has exceeded a predetermined threshold; and transmitting data associated with the cumulative radiation dose received by the photodiode.

13. The device of claim 12, wherein wireless interface is compliant to a least one version of a Bluetooth communication protocol.

14. The device of claim 12, wherein the device is implemented within at least one of a light dosimeter and a power meter.

15. The device of claim 12, wherein the photodiode is an Aluminum Gallium Nitride based Schottky diode.

16. A device comprising:

a photodiode;

a narrowband optical filter having a passband of at least 250 nanometers to 260 nanometers;

an integrating capacitor electrically coupled with the photodiode;

a voltage discharge switch electrically coupled with the integrating capacitor; and amplifier circuitry electrically coupled with the photodiode and the integrating capacitor, wherein:

the photodiode is configured for detecting ultraviolet-C radiation;

the amplifier circuitry is configured to maintain a substantially zero bias voltage between an anode and a cathode of the photodiode while monitoring cumulative radiation;

the integrating capacitor is configured to provide a delta voltage representative of radiation received during a charge cycle of the integrating capacitor; and the narrowband optical filter is integrated with the photodiode.

17. The device of claim 16, wherein the device is implemented within at least one of a light dosimeter and a power meter.

18. The device of claim 16, wherein the photodiode is an Aluminum Gallium Nitride based Schottky diode.

19. A device comprising:

a photodiode;

a narrowband optical filter having a passband of at least 220 nanometers to 280 nanometers;

an integrating capacitor electrically coupled with the photodiode;

a voltage discharge switch electrically coupled with the integrating capacitor; and amplifier circuitry electrically coupled with the photodiode and the integrating capacitor, wherein:

the photodiode is configured for detecting ultraviolet-C radiation;

the amplifier circuitry is configured to maintain a substantially zero bias voltage between an anode and a cathode of the photodiode while monitoring cumulative radiation;

the integrating capacitor is configured to provide a delta voltage representative of radiation received during a charge cycle of the integrating capacitor; and the narrowband optical filter is integrated with the photodiode.

20. The device of claim 19, wherein the device is implemented within at least one of a light dosimeter and a power meter.

21. The device of claim 19, wherein the photodiode is an Aluminum Gallium Nitride based Schottky diode.

22. A method of operating a device for measuring cumulative radiation, the method comprising:

charging an integrating capacitor using a photodiode, wherein a voltage across the integrating capacitor is representative of radiation received during a charge cycle of the integrating capacitor;

maintaining a substantially zero bias voltage between an anode and a cathode of the photodiode using amplifier circuitry electrically coupled with the photodiode and the integrating capacitor;

determining when the voltage across the integrating capacitor has crossed a predetermined threshold;

discharging the voltage across the integrating capacitor using a voltage discharge switch electrically coupled with the integrating capacitor upon receiving a reset signal;

maintaining a count of a plurality of discharge cycles of the integrating capacitor; and displaying on a user interface an estimate of a radiation dose received by a surface based on the count of the plurality of discharge cycles of the integrating capacitor.

* * * * *